United States Patent [19]

Wivell et al.

[11] Patent Number: 5,599,549
[45] Date of Patent: *Feb. 4, 1997

[54] COMBINED PERSONAL CLEANSING AND MOISTURIZING COMPOSITIONS

[75] Inventors: Susan C. Wivell, Madison; George E. Deckner, Trumbull, both of Conn.

[73] Assignee: Richardson-Vicks Inc., Shelton, Conn.

[ * ] Notice: The term of this patent shall not extend beyond the expiration date of Pat. No. 5,439,682.

[21] Appl. No.: 437,479

[22] Filed: May 9, 1995

Related U.S. Application Data

[62] Division of Ser. No. 35,517, Mar. 22, 1993, Pat. No. 5,439,682, which is a continuation of Ser. No. 797,519, Nov. 22, 1991, abandoned.

[51] Int. Cl.$^6$ .............................. A61K 6/00; A61K 7/00
[52] U.S. Cl. ................................ 424/401; 424/70.1
[58] Field of Search ........................ 424/401, 405, 424/1.13, 70.1

[56] References Cited

U.S. PATENT DOCUMENTS

| | | | |
|---|---|---|---|
| 3,962,150 | 6/1976 | Viola | 252/542 |
| 3,974,208 | 8/1976 | Dudzinski et al. | 562/553 |
| 4,310,433 | 1/1982 | Stiros | 252/DIG. 5 X |
| 4,490,355 | 12/1984 | Desai | 252/DIG. 5 X |
| 4,617,148 | 10/1986 | Shields | 252/547 |
| 4,620,878 | 11/1986 | Gee | 252/174.15 |
| 4,663,158 | 5/1987 | Wolfram et al. | 424/70 |
| 4,690,818 | 9/1987 | Puchalski et al. | 424/70 |
| 4,717,498 | 1/1988 | Maxon | 252/174.15 |
| 4,726,915 | 2/1988 | Verdicchio | 252/542 |
| 4,954,332 | 9/1990 | Bissett et al. | 424/59 |
| 4,963,535 | 10/1990 | Sebag et al. | 514/54 |
| 4,976,953 | 12/1990 | Orr et al. | 424/424 |
| 5,002,680 | 3/1991 | Schmidt et al. | 252/DIG. 5 X |
| 5,011,681 | 4/1991 | Ciotti | 252/174.15 |
| 5,084,270 | 1/1992 | Ciaudelli | 424/59 |
| 5,118,507 | 6/1992 | Clement | 424/401 |
| 5,132,037 | 7/1992 | Greene et al. | 252/108 |

OTHER PUBLICATIONS

11—Package and Advertising Copy, "Avon Moisture Therapy Body Cleanser", Avon Products, Inc. (New York, NY: 1990).

*Primary Examiner*—Thurman K. Page
*Assistant Examiner*—William E. Benston, Jr.
*Attorney, Agent, or Firm*—Anthony D. Sabatelli; David K. Dabbiere

[57] ABSTRACT

The present invention relates to compositions which provide both a skin cleansing and skin moisturizing benefit from the same product. These compositions provide improved lathering and cleansing characteristics, are extremely mild to the skin, and deliver a moisturizing agent to the skin. These compositions comprise at least one anionic surfactant, a dispersed, insoluble oil phase, at least one additional surfactant, an optional suspending agent, and water. This invention also relates to methods for providing combined cleansing and moisturization, and to methods for delivering these compositions as a foam.

1 Claim, No Drawings

COMBINED PERSONAL CLEANSING AND MOISTURIZING COMPOSITIONS

This is a division of application Ser. No. 08/035,517, filed on Mar. 22, 1993, now U.S. Pat. No. 5,439,682 which is a continuation of application Ser. No. 07/797,519, filed on Nov. 22, 1991.

TECHNICAL FIELD

The present invention relates to compositions which provide both a skin cleansing and skin moisturizing benefit from the same product. These compositions provide improved lathering and cleansing characteristics, are extremely mild to the skin, and upon rinse-off deliver a moisturizing agent to the skin. These compositions comprise at least one anionic surfactant, a dispersed, insoluble oil phase, at least one additional surfactant selected from nonionic, zwitterionic and amphoteric surfactants, an optional suspending agent, and water. This invention also relates to methods for providing combined cleansing and moisturization, and to methods for delivering these compositions as a foam.

BACKGROUND OF THE INVENTION

Cleansing compositions must satisfy a number of criteria including cleansing power, foaming properties, and mildness/low irritancy with respect to the skin, hair and the occular mucosae.

Skin is made up of several layers of cells which coat and protect the keratin and collagen fibrous proteins that form the skeleton of its structure. The outermost of these layers, referred to as the stratum corneum, is known to be composed of 250 Å diameter protein bundles surrounded by 80 Å thick bilayers of epidermal lipids and water. Anionic surfactants can penetrate the stratum corneum membrane and, by delipidization (i.e. removal of the lipids from the stratum corneum), destroy its integrity. This destruction of the stratum corneum bilayers can lead to dry rough skin and may eventually permit the surfactant to interact with the viable epidermis, creating irritation.

Ideal cosmetic cleansers should cleanse the skin gently, causing little or no irritation without defatting and or drying the skin and without leaving skin taut after frequent use. Most lathering soaps, liquids and bars fail in this respect. Also, most current cleansing products do not deliver an adequate moisturizing benefit during cleansing. Therefore, users typically must moisturize their skin in a separate step following cleansing.

Certain synthetic surfactants are known to be mild. However, a major drawback of most mild synthetic surfactant systems, when formulated for skin cleansing, is poor lather performance compared to the highest bar soap standards (bars which are rich in coconut soap and superfatted). On the other hand, the use of known high sudsing anionic surfactants with lather boosters can yield acceptable lather volume and quality. Unfortunately, however, the highest sudsing anionic surfactants are, in fact, poor in clinical skin mildness. Surfactants that are among the mildest, such as sodium lauryl glyceryl ether sulfonate, (AGS), are marginal in lather. These two facts make the balancing of the surfactant selection and the lather and skin feel benefit a delicate process. Rather stringent requirements for cosmetic cleansers limit the choice of surface-active agents, and final formulations represent some degree of compromise. Mildness is often obtained at the expense of effective cleansing, or lathering may be sacrificed for either mildness, product stability, or both.

Furthermore, it would be highly desirable to also deliver skin moisturizers from cleansing compositions, because this would provide users with the convenience of obtaining both a cleansing and a moisturizing benefit from a single product. However, such dual cleansing and moisturizing compositions are difficult to formulate because the cleansing ingredients, in general, tend to be incompatible with the moisturizing ingredients.

Thus a need exists for cleansing compositions which will produce a foam which is abundant, stable and of high quality (compactness), which are effective skin cleansers, which are very mild to the skin and occular mucosae, and which can also deliver a moisturizing agent to the skin. These combined skin cleansing and moisturizing compositions would be termed two-in-one cleansers because of the dual cleansing and moisturizing benefits they would provide.

One highly successful solution to this dilemma of delivering both a cleansing and conditioning benefit from the same product has been in the shampoo area. Two-in-one conditioning shampoos have been developed which deliver suspended silicone hair conditioning agents in the presence of various cleansing surfactants. See U.S. Pat. No. 4,788,006, to Bolich, Jr. et al., issued Nov. 29, 1988; U.S. Pat. No. 4,741,855, to Grote et al, issued May 3, 1988; and U.S. Pat. No. 4,704,272, to Oh et al., issued Nov. 3, 1987. Shampoos, though, generally contain higher levels of more potent surfactants than are needed or desirable for gently cleansing the skin, because the hair has a larger surface area compared to the skin and tends to become soiled with higher levels of sebum, dirt, and other debris. Conversely, the hair generally requires much lower levels of conditioners than the skin, because the hair is easily overconditioned resulting in limp, unmanageable, and resoiled hair. Thus, it is seen that cleansing and moisturizing the skin is different from cleansing and conditioning the hair. Therefore, it would be highly desirable to develop effective, yet gentle, skin cleansing compositions which would also provide a skin moisturizing benefit.

It is therefore an object of the present invention to provide improved personal cleansing compositions which thoroughly cleanse the skin and which also moisturize the skin, i.e. to provide combined skin cleansing and moisturizing compositions.

It is a further object of the present invention to provide combined cleansing and moisturizing compositions which are very mild to the skin and occular mucosae.

It is an even further object of the present invention to provide combined cleansing and moisturizing compositions which will produce a foam which is abundant, stable, and of high quality.

It is a still further object of the present invention to provide methods for cleansing and moisturizing the skin.

It is a yet further object of the present invention to provide methods for delivering combined cleansing and moisturizing compositions as foams.

These and other objects will become readily apparent from the detailed description which follows.

SUMMARY OF THE INVENTION

The present invention relates to a personal cleansing composition comprising:

(a) from about 1% to about 10% of at least one anionic surfactant, (b) from 0% to about 15% of a suspending agent, (c) from about 0.1% to about 10% of a dispersed, insoluble, oil phase, (d) from about 1% to about 10% of at least one additional surfactant selected from the group consisting of nonionic surfactants, zwitterionic surfactants, amphoteric surfactants, and mixtures thereof, and (e) the remainder water.

The present invention further relates to methods for cleansing and moisturizing the skin and to methods for delivering these cleansing compositions as a dense, compact foam.

All percentages and ratios used herein are by weight or by a solids weights basis and all measurements are at 25° C., unless otherwise indicated.

DETAILED DESCRIPTION OF THE INVENTION

The present invention relates to compositions which provide both a skin cleansing and skin moisturizing benefit from the same product. It has been found that compositions comprising certain anionic surfactants in combination with at least one additional surfactant selected from nonionic, zwitterionic, and amphoteric surfactants, provide good cleansing and foaming and yet are mild to the skin. Further, it has been found that insoluble, oil phase moisturizing agents can be dispersed in these compositions employing an optional suspending agent to provide a moisturizing benefit from the cleanser.

Essential Ingredients

Anionic Surfactants

The combined personal cleansing and moisturizing compositions herein comprise at least from about 0.1% to about 70%, preferably from about 1% to about 10%, and most preferably from about 2% to about 7.5% of at least one anionic surfactant.

Anionic surfactants useful herein include ethoxylated alkyl sulfates, alkanoyl sarcosinates, and mixtures thereof. The ethoxylated alkyl sulfates correspond to the formula $RO(C_2H_4O)_xSO_3M$ wherein R is alkyl or alkenyl of about 10 to about 20 carbon atoms, x is 1 to 10, and M is a water-soluble cation such as ammonium, sodium, potassium and trialkanolamine (e.g., triethanolamine). The preferred ethoxylated alkyl sulfates useful in the present invention are condensation products of ethylene oxide and monohydric alcohols having about 10 to about 20 carbon atoms. Preferably, R has about 14 to about 18 carbon atoms. The alcohols can be derived from fats, e.g. coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species is sulfated and neutralized. An especially preferred ethoxylated alkyl sulfate for use herein is sodium laureth-3 sulfate.

The alkanoyl sarcosinates correspond to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine). Preferably, R has about 14 to about 18 carbon atoms. An especially preferred alkanoyl sarcosinate for use herein, is sodium lauroyl sarcosinate.

Additional Surfactants

The combined personal cleansing and moisturizing compositions herein comprise at least from about 0.1% to about 70%, preferably from about 1% to about 10%, and most preferably from about 2% to about 8% of at least one additional surfactant selected from the group consisting of nonionic surfactants, zwitterionic surfactants, amphoteric surfactants, and mixtures thereof.

Suitable surfactants are disclosed in McCutcheon's, *Detergents and Emulsifiers*, North American Edition (1986), published by Allured Publishing Corporation; U.S. Pat. No. 5,011,681, to Ciotti et al., issued Apr. 30, 1991; U.S. Pat. No. 4,788,006, to Bolich, Jr. et al., issued Nov. 29, 1988; U.S. Pat. No. 4,741,855, to Grote et al., issued May 3, 1988; U.S. Pat. No. 4,704,272, to Oh et al., issued Nov. 3, 1987; U.S. Pat. No. 4,421,769, to Dixon et al, issued Dec. 20, 1983; and U.S. Pat. No. 3,755,560, to Dickert et al, issued Aug. 28, 1973; each of which is incorporated herein by reference in its entirety.

Preferred additional surfactants include ethoxylated glyceryl esters, alkanoylamidopropyl betaines, alkanoylamido hydroxysultaines, and mixtures thereof. Especially preferred are the PEG glyceryl fatty acid derivatives such as PEG-20 glyceryl stearate, PEG-80 glyceryl tallowate, PEG-30 glyceryl cocoate, PEG-80 glyceryl cocoate, and PEG-200 glyceryl tallowate (available as the Varonic LI series from Sherex); betaines such as cocamidopropyl betaine (available as Velvetex BK-35 and BA-35 from Henkel); hydroxysultaines such as cocamidopropyl hydroxysultaine (available as Mirataine CBS from Rhone-Poulenc), and mixtures thereof.

Dispersed, Insoluble Oil Phase

The combined personal cleansing and moisturizing compositions herein comprise at least from about 0.1% to about 10%, preferably from about 0.5% to about 5%, and most preferably from about 0.75% to about 2% of a dispersed, insoluble oil phase.

Without being limited by theory it is believed that this oil phase of the compositions of the instant invention provides a skin moisturizing benefit by depositing upon the skin during the cleansing and rinsing processes. By "dispersed" is meant that the oil phase can exist as a separate and distinct phase of fine particles, aggregates, or liquid crystals within the water phase of the compositions of the instant invention. By "insoluble" is meant that the oil phase has a solubility of less than about 5.0 grams per 100 grams of water at 25° C., preferably less than about 1.0 gram per 100 grams of water at 25° C.

A wide variety of oil type and emollient type materials and mixtures of materials are suitable for use in the oil phase of the compositions of the present invention. Preferably, the oil phase is selected from the group consisting of silicones, hydrocarbons, fatty acids, fatty acid derivatives, cholesterol, cholesterol derivatives, vegetable oils, vegetable oil derivatives, and mixtures thereof.

Examples of silicones include non-volatile silicones such as dimethicone copolyol; dimethylpolysiloxane; diethylpolysiloxane; high molecular weight dimethicone (average molecular weight from about 200,000 to about 1,000,000 and, preferably, from about 300,000 to about 600,000) which can have various end-terminating groups such as hydroxyl, lower $C_1$–$C_3$ alkyl, lower $C_1$–$C_3$ alkoxy and the like; mixed $C_1$–$C_3$ alkyl polysiloxane (e.g., methylethylpolysiloxane); phenyl dimethicone and other aryl dimethicones; dimethiconol; fluorosilicones; and mixtures thereof.

Preferred are non-volatile silicones selected from the group consisting of dimethicone copolyol, dimethylpolysiloxane, diethylpolysiloxane, high molecular weight dimethicone, mixed $C_1$–$C_{30}$ alkyl polysiloxane, phenyl dimethicone, dimethiconol, and mixtures thereof. More preferred are non-volatile silicones selected from dimethicone, dimethiconol, mixed $C_1$–$C_{30}$ alkyl polysiloxane, and mixtures thereof. Especially preferred is dimethiconol which is a dimethyl silicone polymer terminated with hydroxyl groups. Dimethiconol is available as Q2-1401 Fluid, a solution of 13 percent ultra-high-viscosity dimethiconol in volatile cyclomethicone fluid as a carrier; as Q2-1403 Fluid, a solution of ultra-high-viscosity dimethiconol fluid in dimethicone (both sold by Oow Corning Corporation); and as other custom blends (e.g. 10% dimethiconol in dimethicone). Nonlimiting examples of silicones useful herein are described in U.S. Pat. No. 5,011,681, to Ciotti et al., issued Apr. 30, which has already been incorporated by reference.

Examples of hydrocarbons include materials such as petrolatum, mineral oil (e.g., USP light or heavy), and branched hydrocarbons (e.g., isohexadecane, available as Permethyl 101A from Presperse).

Examples of fatty acids and fatty acid derivatives include esters such as diisopropyl adipate, isopropyl myristate, isopropyl palmitate, ethylhexyl palmitate, isodecyl neopentanoate, C12–15 alcohols benzoate, diethylhexyl maleate, PPG-14 butyl ether, PPG-2 myristyl ether propionate, and the like. Especially preferred are long chain esters of long chain fatty acids, e.g. cetyl ricinoleate.

Examples of cholesterol and cholesterol derivatives include cholesterol, and cholesterol esters and ethers (e.g., cholesterol stearte, cholesterol isosterate, cholesterol acetate, and the like).

Examples of vegetable oils and vegetable oil derivatives include, soybean oil, derivatized soybean oils such as maleated soybean oil, coconut oil and derivatized coconut oil, cottonseed oil and derivatized cottonseed oil, jojoba oil, cocoa butter, and the like.

Examples of other materials useful in the oil phase include other natural and synthetic triglycerides, lanolin, lanolin esters and derivatives, animal fats, and other synthetic fats and oils. Examples of other suitable-materials, including emollients, are disclosed in U.S. Pat. No. 4,919,934, to Deckner et al., issued Apr. 24, 1990; which is incorporated herein by refernce.

Water

The moisturizing and cleansing compositions of the present invention comprise water as an essential component. The water is present from about 50); to about 99.7%, preferably from about 60% to about 80%, and most preferably from about 65% to about 75%.

Optional Ingredients

Suspending Agent

A highly preferred optional component of the present compositions is a suspending agent or mixture of suspending agents. The suspending agent or mixture of agents is present at a level of from about 0% to about 15%, preferably from about 0.4% to about 15%, and more preferably from about 5% to about 15%. The optional suspending agent serves to assist in suspending the insoluble oil phase and may also give pearlescence to the product. Preferred materials are long chain acyl derivatives as well as other long chain materials, and xanthan gum. Especially preferred are long chain acyl derivatives as well as other long chain materials.

Suspending agents useful in the present compositions are any of several long chain ($C_{16-22}$) acyl derivative materials such as those selected from the group consisting of ethylene glycol long chain esters, alkanol amides of long chain fatty acids, long chain esters of long chain fatty acids, glyceryl long chain esters, long chain esters of long chain alkanol amides, and mixtures thereof. Included are ethylene glycol esters of fatty acids having from about 16 to about 22 carbon atoms. Preferred are the ethylene glycol stearates, both mono and distearate, but particularly the distearate containing less than about 7% of the monostearate. Other suspending agents found useful are alkanolamides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate.

Another suspending agent useful in the present compositions is xanthan gum. This biosynthetic gum material is commercially available and is a heteropolysaccharide with a molecular weight of greater than 1 million. it contains D-glucose, D-mannose and D-glucuronate in the molar ratio of 2.8:2.0:2.0. The polysaccharide is partially acetylated with 4.7% acetyl. This information and other information is found in Whistler, Roy L. Editor *Industrial Gums—Polysaccharides and Their Derivatives* New York: Academic Press, 1973, which is incorporated herein by reference. Kelco, a Division of Merck & Co., Inc. offers xanthan gum as Keltrol$^R$.

Useful suspending agents are described in U.S. Pat. No. 4,788,006, to Bolich, Jr. et al., issued Nov. 29, 1988; U.S. Pat. No. 4,741,855, to Grote et al., issued May 3, 1988; and U.S. Pat. No. 4,704,272, to Oh et al., issued Nov. 3, 1987; all of which have already been incorporated herein by reference.

Humectants

The compositions of the instant invention can optionally contain one or more humectants and/or skin moisturizers. A variety of humectants and/or moisturizers can be employed and can be present at a level of from about 0.1% to about 20%, more preferably from about 0.5% to about 5%, and most preferably from about 2% to about 4%. These materials include, but are not limited to, urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol ( including D-, L-, and the D,L-forms); pyrrolidone carboxylic acid; hyaluronic acid; lactamide monoethanolamine; acetamide monoethanolamine; and mixtures thereof.

Preferred humectants for use in the compositions of the present invention are the $C_3$–$C_6$ diols and triols. Especially preferred is the triol, glycerol.

Optional Surfactants

The compositions of the instant invention can optionally contain one or more additional surfactant materials. A variety of additional surfactants can be employed and can be present at a level of from about 0.1% to about 10%, more preferably from about 0.5% to about 5%, and most preferably from about 2% to about 4%.

Suitable optional surfactants can include any of a wide variety of nonionic, cationic, anionic, and zwitterionic surfactants, such as those disclosed in McCutcheon's, *Detergents and Emulsifiers*, North American Edition (1986), published by Allured Publishing Corporation; U.S. Pat. No. 5,011,681, to Ciotti et al., issued Apr. 30,1991; U.S. Pat. No. 4,421,769, to Dixon et al, issued Dec. 20, 1983; and U.S. Pat. No. 3,755,560, to Dickert et al, issued Aug. 28, 1973;

each of which has already been incorporated herein by reference.

Other Optional Components

A variety of additional ingredients can be incorporated into the compositions of the present invention. Nonlimiting examples of these additional ingredients include vitamins and derivatives thereof (e.g., ascorbic acid, vitamin E, tocopheryl acetate, and the like); sunscreens; thickening agents (e.g., polyol alkoxy ester, available as Crothix from Croda); cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc); carboxylic copolymers (e.g., carbomers); emulsifiers; emollients; preservatives for maintaining the antimicrobial integrity of the compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates pigments, pearlescent agents (e.g., mica and titanium dioxide), lakes, colorings, and the like (e.g., clove oil, menthol, camphor, eucalyptus oil, and eugenol ). Nonlimiting examples of suitable carboxylic copolymers, emulsifiers, emollients, and other additional ingredients are disclosed in U.S. Pat. No. , 5,011,681, to Ciotti et al., issued Apr. 30, 1991, which has already been incorporated by reference herein.

Methods for Cleansing and Moisturing the Skin

The compositions of the instant invention are useful for cleansing and moisturizing the skin. Typically, a suitable amount of the composition is directly applied to the skin, which has optionally been premoistened with water. Alternatively, a suitable amount of the composition can be applied to the skin via intermediate application to the hands, a washcloth, a sponge, or other application device. It has been found that the compositions of the instant invention provide their optimal cleansing performance when combined with water during the cleansing process. To complete the cleansing process, the compositions of the instant invention are thoroughly rinsed from the skin with water, thereby leaving behind the moisturizing ingredients. Suitable amounts of the composition for use in cleansing range from, but are not limited to, about 0.5 mg/cm$^2$ to about 5.0 mg/cm$^2$ of skin area.

Other Product Forms

The compositions of the instant invention can be suitably formulated as foaming gels, foaming lotions, foaming scrubs, and the like.

Delivery of the Compositions as a Foam

In further embodiments, the compositions of the instant invention can be delivered as a foam. Preferably the foam has a density of from about 0.01 gms/cm$^3$ to about 0.25 gms/cm$^3$, more preferably from about 0.05 gms/cm$^3$ to about 0.20 gms/cm$^3$, and most preferably from about 0.08 gms/cm$^3$ to about 0.11 gms/cm$^3$.

For delivery as a foam, the compositions of the instant invention can be delivered, for example, from a hand-held device such as a nonaerosol pump roamer or from an aerosol container charged with a suitable propellant system.

Non-aerosol squeeze roamer packages are well known as exemplified by the disclosures in the following patents that are incorporated herein by reference. U.S. Pat. No. 3,709,437, to Wright, issued Jan. 9, 1973; U.S. Pat. No. 3,937,364, to Wright, issued Feb. 10, 1976; U.S. Pat. No. 4,022,351, to Wright, issued May 10, 1977; U.S. Pat. No. 4,147,306, to Bennett, issued Apr. 3, 1979, U.S. Pat. No. 4,184,615, to Wright, issued Jan. 22, 1980; U.S. Pat. No. 4,598,862, to Rice, issued Jul. 8, 1986; U.S. Pat. No. 4,615,467, to Grogan et al., issued Oct. 7, 1986; and French Patent No. 2,604,622, to Verhulst, published Apr. 8, 1988, These containers (packages) do not use any propellant. They create a foam from almost any surfactant composition. The composition is placed in the container reservoir (plastic squeeze bottle). Squeezing the container with the hand forces the composition through a roamer head, or other foam producing means, where the composition is mixed with air and then through a homogenizing means that makes the foam more homogeneous and controls the consistency of the foam. The foam is then discharged as a uniform, non-pressurized aerated foam.

Pressurized aerosol delivery systems are also well-known in the art. When the compositions of the instant invention are delivered from such pressurized systems, the compositions further comprise from about 25% to about 80%, preferably from about 30% to about 50%, of suitable propellants. Examples of such propellants are the chlorinated, fluorinated, and chlorofluorinated lower molecular weight hydrocarbons; nitrous oxide; carbon dioxide; butane; propane; and the like. These propellants are used at a level sufficient to expel the contents of the container.

When the compositions of the instant invention are optionally delivered as a foam, it is preferable that the composition used for such delivery has a viscosity in the range from about 0.1 cPs to about 40 cPs, preferably from about 1 cPs to about 30 cPs, and most preferably from about 10 cPs to about 20 cPs. These viscosities are determined at 25° C. using a Brookfield RVT (Brookfield Instruments, Stoughton, Mass.) equipped with a spindle No. 1 at 100 rpm.

EXAMPLE

The following examples further describe and demonstrate the preferred embodiments within the scope of the present invention. The examples are given solely for the purpose of illustration, and are not to be construed as limitations of the present invention, since many variations thereof are possible without departing from its spirit and scope.

Ingredients are identified by chemical or CTFA name.

Example I

A combined cleansing and moisturizing composition containing a dispersed oil phase comprising a mixture of a hydrocarbon and a fatty acid derivative is prepared by combining the following ingredients.

| Ingredients | Weight Percent |
| --- | --- |
| Phase A | |
| Water | QS100 |
| Guar Hydroxypropyltrimonium chloride | 0.75 |
| Citric Acid | 0.00–2.00 |
| Phase B | |
| Sodium Lauroyl Sarcosinate | 3.94 |
| Cocamidopropyl Hydroxysultaine | 1.31 |
| Cocamidopropyl Betaine | 0.70 |

| Ingredients | Weight Percent |
|---|---|
| PEG-80 Glyceryl Cocoate | 4.38 |
| Citric Acid | 0.17 |
| Ethylene Glycol Distearate | 10.0 |
| Phase C | |
| PEG-80 Glyceryl Cocoate | 1.40 |
| Phase D | |
| Petrolatum | 0.50 |
| Cetyl Ricinoleate | 0.50 |
| Sodium Laureth Sulfate | 0.26 |
| Sodium Chloride | 0.05 |
| Phase E | |
| Ricinoleoamidopropyltrimonium Chloride (and) Propylene Glycol | 1.28 |
| Polyquaternium-2 | 0.75 |
| Phase F | |
| Cocamidopropyl Hydroxysultaine | 1.02 |
| Phase G | |
| Cocamidopropyl Betaine | 1.02 |
| Phase H | |
| Phenoxyethanol | 0.40 |
| DMDM Hydantoin | 0.08 |
| Mica (and) Titanium Dioxide | 0.10 |
| Fragrance | 0.15 |
| Phase I | |
| Sodium Hydroxide | 0.00–2.00 |

The water and guar hydroxypropyltrimonium chloride are combined to form a homogeneous solution and heated to 70° C. Next the pH is adjusted to 3.0–6.0 with citric acid as needed and the mixture (Phase A) is cooled to room temperature. Next, the Phase B ingredients are combined with heating to 80° C. until homogeneous, cooled to room temperature, and added to Phase A. Each of Phases C through H is then separately prepared by mixing at room temperature and sequentially added to the composition with mixing. Finally, the resulting mixture is adjusted to pH 6.0–7.0 with sodium hydroxide as needed.

The resulting combined cleansing and moisturizing composition is useful for cleansing and moisturizing the skin.

Example II

A combined cleansing and moisturizing composition containing a dispersed oil phase comprising maleated soybean oil is prepared by combining the following ingredients.

| Ingredients | Weight Percent |
|---|---|
| Phase A | |
| Water | QS100 |
| Guar Hydroxypropyltrimonium chloride | 0.75 |
| Citric Acid | 0.00–2.00 |
| Phase B | |
| Sodium Lauroyl Sarcosinate | 3.94 |
| Cocamidopropyl Hydroxysultaine | 1.31 |
| Cocamidopropyl Betaine | 0.70 |
| PEG-80 Glyceryl Cocoate | 4.38 |
| Citric Acid | 0.17 |
| Ethylene Glycol Distearate | 10.0 |
| Phase C | |
| PEG-80 Glyceryl Cocoate | 1.40 |
| Phase D | |
| Maleated Soybean Oil | 1.00 |
| Sodium Laureth Sulfate | 0.26 |
| Sodium Chloride | 0.05 |
| Phase E | |
| Ricinoleoamidopropyltrimonium Chloride (and) Propylene Glycol | 1.28 |
| Polyquaternium-2 | 0.75 |
| Phase F | |
| Cocamidopropyl Hydroxysultaine | 1.02 |
| Phase G | |
| Cocamidopropyl Betaine | 1.02 |
| Phase H | |
| Phenoxyethanol | 0.40 |
| DMDM Hydantoin | 0.08 |
| Mica (and) Titanium Dioxide | 0.10 |
| Fragrance | 0.15 |
| Phase I | |
| Sodium Hydroxide | 0.00–2.00 |

The composition is prepared using the general procedure given in Example I.

The resulting combined cleansing and moisturizing composition is useful for cleansing and moisturizing the skin.

Example III

A combined cleansing and moisturizing composition containing a dispersed oil phase comprising nonvolatile silicones is prepared by combining the following ingredients.

| Ingredients | Weight Percent |
|---|---|
| Phase A | |
| Water | QS100 |
| Guar Hydroxypropyltrimonium chloride | 0.75 |
| Citric Acid | 0.00–2.00 |
| Phase B | |
| Sodium Lauroyl Sarcosinate | 3.94 |
| Cocamidopropyl Hydroxysultaine | 1.31 |
| Cocamidopropyl Betaine | 0.70 |
| PEG-80 Glyceryl Cocoate | 4.38 |
| Citric Acid | 0.17 |
| Ethylene Glycol Distearate | 10.0 |
| Phase C | |
| PEG-80 Glyceryl Cocoate | 1.40 |
| Phase D | |
| Dimethicone (and) Dimethiconol[1] | 1.00 |
| Sodium Laureth Sulfate | 0.26 |
| Sodium Chloride | 0.05 |
| Phase E | |
| Cocamidopropyl Hydroxysultaine | 1.02 |
| Phase F | |
| Cocamidopropyl Betaine | 1.02 |
| Phase G | |
| Phenoxyethanol | 0.40 |
| DMDM Hydantoin | 0.08 |
| Mica (and) Titanium Dioxide | 0.10 |
| Fragrance | 0.15 |

-continued

| Ingredients | Weight Percent |
| --- | --- |
| Phase H | |
| Sodium Hydroxide | 0.00–2.00 |

¹Available as Dow Corning Q2-1403. Alternatively, a custom blend of dimethiconol (for example 10%) in dimethicone can be employed.

The composition is prepared using the general procedure given in Example I, with the only change being one less phase to be added.

The resulting combined cleansing and moisturizing composition is useful for cleansing and moisturizing the skin.

Example IV

A combined cleansing and moisturizing composition, without a suspending agent, and containing a dispersed oil phase comprising maleated soybean oil is prepared by combining the following ingredients.

| Ingredients | Weight Percent |
| --- | --- |
| Phase A | |
| Water | QS100 |
| Phase B | |
| Sodium Lauroyl Sarcosinate | 2.25 |
| Cocamidopropyl Hydroxysultaine | 3.25 |
| Cocamidopropyl Betaine | 2.25 |
| PEG-80 Glyceryl Cocoate | 2.25 |
| Phase C | |
| Maleated Soybean Oil | 1.25 |
| Linoleamidopropyl PG-Dimonium Chloride Phospate | 1.00 |
| Phase D | |
| Water | 2.00 |
| Polyquaternium-2 | 0.75 |
| Cocamidopropyl Hydroxysultaine | 0.25 |
| Cocamidopropyl Betaine | 0.25 |
| Phase E | |
| Polyol alkoxy ester | 1.00 |
| Phase F | |
| Phenoxyethanol | 0.40 |

| Ingredients | Weight Percent |
| --- | --- |
| DMDM Hydantoin | 0.08 |
| Mica (and) Titanium Dioxide | 0.10 |
| Fragrance | 0.15 |
| Phase I | |
| Triethanolamine | 0.00–2.00 |

Phases A, B, and C are each prepared at room temperature, and these three phases are combined with mixing until clear. Phase D is prepared and added to the mixture, which is then heated to 80° C. Next, Phase E is added with mixing, and the mixture is then cooled to room temperature. Phase F is prepared and added with mixing. Finally, the mixture is adjusted to pH 6.0–7.0 with the triethanolamine as needed.

The resulting combined cleansing and moisturizing composition is useful for cleansing and moisturizing the skin.

What is claimed is:

1. A method for delivering to the skin a cleansing and moisturizing composition, wherein said composition is delivered from a non-aerosol mechanical pump as an aerated foam having a density from about 0.01 gms/cm$^3$ to about 0.25 gms/cm$^3$, said composition, comprising:

(a) from about 1% to about 10% of at least one anionic surfactant,
   (b) from about 0.4% to about 15% of a long chain C16–22 suspending agent selected from the group consisting of ethylene glycol long chain esters, alkanolamides of long chain fatty acids, long chain esters of long chain fatty acids, glyceryl long chain esters, long chain esters of long chain alkanolamides, and mixtures thereof,
   (c) from about 0.1% to about 10% of a dispersed, insoluble, oil phase,
   (d) from about 1% to about 10% of at least one additional surfactant selected from the group consisting of nonionic surfactants, zwitterionic surfactants, amphoteric surfactants, and mixtures thereof, and
   (e) the remainder water, and wherein said composition has a viscosity from about 0.1 cPs to about 40 cPs as measured at 25° C. using a Brookfield RVT equipped with a Spindle No. 1, at 100 rpm.

* * * * *

UNITED STATES PATENT AND TRADEMARK OFFICE
CERTIFICATE OF CORRECTION

PATENT NO. : 5,599,549

DATED : February 4, 1997

INVENTOR(S) : Susan Ciotti Wivell, George Endel Deckner

It is certified that error appears in the above-identified patent and that said Letters Patent is hereby corrected as shown below:

At column 4, line 56 "dtmethylpolysiloxane" should read --dimethylpolysiloxane--.

At column 5, line 11 "Oow" should read --Dow--.

At column 5, line 39 "suitable-materials" should read --suitable materials--.

At column 5, line 46 "50);" should read --50%--.

At column 5, line 67 "alkanol amides" should read --alkanolamides--.

At column 6, line 2 "alkanol amides" should read --alkanolamides--.

At column 6, line 17 "it" should read --It--.

At column 7, line 30 "Moisturing" should read --Moisturizing--.

At column 7, line 66 "roamer" should read --foamer--.

At column 8, line 1 "roamer" should read --foamer--.

At column 8, line 11 "1988," should read --1988.--.

At column 8, line 16 ""roamer" should read --foamer--.

At column 8, line 40 "EXAMPLE" should read --EXAMPLES--.

Signed and Sealed this

First Day of July, 1997

*Attest:*

BRUCE LEHMAN

*Attesting Officer*  Commissioner of Patents and Trademarks